United States Patent [19]

Yamamura et al.

[11] 4,101,536
[45] Jul. 18, 1978

[54] MURAMYLDIPEPTIDE DERIVATIVES AND PROCESS FOR THE PREPARATION THEREOF

[75] Inventors: Yuichi Yamamura, Hyogo; Tetsuo Shiba, Osaka; Ichiro Azuma, Osaka; Shoichi Kusumoto, Osaka; Tadamasa Hirayama, Tokyo; Tsuneo Kusama, Tokyo, all of Japan

[73] Assignee: Daiichi Seiyaku Co., Ltd., Tokyo, Japan

[21] Appl. No.: 809,245

[22] Filed: Jun. 23, 1977

[30] Foreign Application Priority Data

Jun. 23, 1976 [JP] Japan .............................. 51-74072
Dec. 16, 1976 [JP] Japan .............................. 51-150328
Feb. 3, 1977 [JP] Japan .............................. 52-11122

[51] Int. Cl.$^2$ ..................... C07G 103/52; C07G 7/00; A61K 37/00
[52] U.S. Cl. ............................ 260/112.5 R; 424/177
[58] Field of Search .................. 260/112.5 R; 424/177

[56] References Cited

PUBLICATIONS

Chemical Abstracts, (1975), 83, 206544c.
Wagner, Romeo, Synthetic Organic Chemistry, (1953), John Wiley & Sons, 480.
Asselineau, J., "The Bacterial Lipids," Hermann, Paris, 1966.
Azuma et al., Biken Journal, 17, (1974), pp. 1-3.

Primary Examiner—Delbert R. Phillips
Assistant Examiner—Blondel Hazel
Attorney, Agent, or Firm—Sughrue, Rothwell, Mion, Zinn and Macpeak

[57] ABSTRACT

Muramyldipeptide derivatives of the formula:

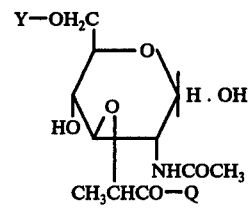

wherein Y represents a mycoloyl group or a synthetic higher acyl group having total carbon number of C30-C90 and having at least a branched chain of long alkyl group on the α-position thereof, Q represents an -L-alanyl-D-isoglutamine group, a -glycyl-D-isoglutamine group or an -L-seryl-D-isoglutamine group;

salts of such derivatives; the method of preparing such derivatives and their salts; the derivatives and their salts having potent immunoadjuvant activities and antitumor activity and being applicable as the agent for the immunotherapy of cancer for humans and animals.

9 Claims, No Drawings

MURAMYLDIPEPTIDE DERIVATIVES AND PROCESS FOR THE PREPARATION THEREOF

BACKGROUND OF THE INVENTION

1. Field of the Invention

This invention relates to novel muramyldipeptide derivatives and to process for preparing the same. More particularly, this invention relates to muramyldipeptide derivatives represented by the general formula (1).

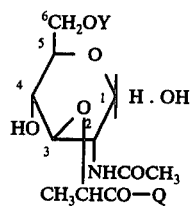

wherein Y represents a mycoloyl group or a synthetic higher acyl group having total carbon number of C30-C90 and having at least a branched chain of long alkyl group on the α-position thereof, and Q represents an -L-alanyl-D-isoglutamine group,
a -glycyl-D-isoglutamine group or
an -L-seryl-D-isoglutamine group.

This invention also relates to salts of such derivatives and to the method of preparing such derivatives and their salts. The compounds have potent immunoadjuvant activity and antitumor activity on syngenic mouse tumor systems such as MH134 hepatoma in $C_3H/He$, and melanoma B16 in C57BL/6J and then being applicable to agents for the immunotherapy of cancer for humans and animals.

2. Description of the prior art

Up to now, it has been reported that bacterial cell wall or the mucopeptide-containing wax D and a peptideglycolipid component of bacterial cell wall have immunoadjuvant activities. As the results of extensive studies on these known substances it has been also revealed that the minimal unit responsible for exhibition of adjuvant activity is N-acetylmuramyl-L-alanyl-D-isoglutamine (hereinafter referred to as "muramyldipeptide"). The muramyldipeptide showed immunoadjuvant activity such as stimulation of increased serum antibody levels and also induction of delayed-type hypersensitivity to an ovalmin protein antigen. It has been further reported by the inventors that 6-O-stearoyl-muramyldipeptide has immunological properties almost similar to those of muramyldipeptide. These two synthetic adjuvants, however, showed no adjuvant activity in the generation of cell-mediated cytotoxic effector cells on the spleen of C57BL/6J mice by the immunization with allogeneic antigen, mastocytoma P815-X2 cell in vivo. Cell-mediated cytotoxic activity closely relates to cellular immune responses and antitumor activity. It has also been demonstrated that these two compounds showed no antitumor activity on syngeneic mouse tumor systems such as MH134 hepatoma in $C_3H/He$ and melanoma B16 in C57BL/6J.

SUMMARY OF THE INVENTION

Accordingly, it is an object of this invention to provide compounds having adjuvant activity in the induction of delayed-type hypersensitivity and in the generation of cell-mediated cytotoxic effector cells on the spleen of C57BL/6J mice by the immunization with allogeneic antigen, mastocytoma P815-X2 cell in vivo, and further having antitumor activity on syngeneic mouse tumor systems such as MH134 hepatoma in $C_3H/He$ and melanoma B16 in C57BL/6J. Another object is to provide methods for preparing such derivatives and their salts. This invention provides muramyldipeptide derivatives represented by the general formula (1)

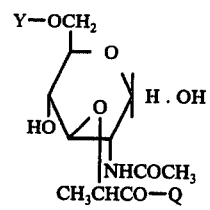

wherein Y represents a mycoloyl group or a synthetic acyl group having total carbon number of C30 -C90 and having at least a branched chain of long alkyl group on the α-position thereof, Q represents an -L-alanyl-D-isoglutamine group,
a -glycyl-D-isoglutamine group or
an -L-seryl-D-isoglutamine group;

the salts of these muramyldipeptide derivatives and methods for the preparation thereof. The compound of this invention can be prepared according to the method represented by the following reaction schematics

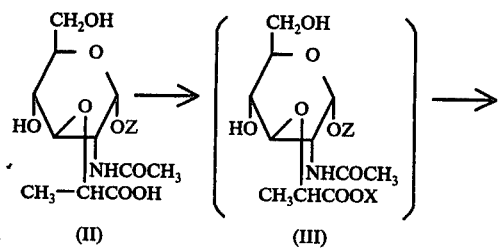

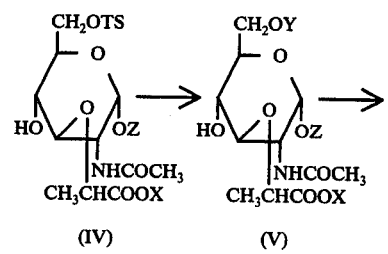

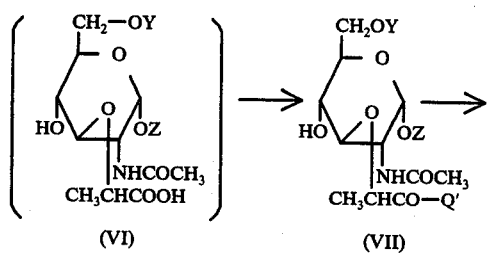

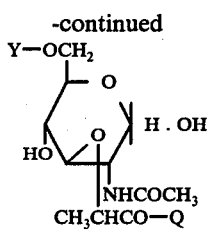

(I)

In the above reaction schematic, the generic symbols which are employed have the following meaning.

Z can be a benzyl group which may have a halogen atom, a nitro group or a lower-alkoxy group, X can be a protective group for carboxyl group such as tertiary butyl group or a diphenylmethyl group, Y can be a mycoloyl group and a synthetic higher acyl group having total carbon number of C30-C90 and having at least a long branched chain of alkyl group on the α-position thereof, Q can be an -L-alanyl-D-isoglutamine group, a -glycyl-D-isoglutamine group or an -L-seryl-D-isoglutamine group, Q' can be a protective L-alanyl-D-isoglutamine group, a protective glycyl-D-isoglutamine group or a protective L-seryl-D-isoglutamine group.

DETAILED DESCRIPTION OF THE INVENTION

The compounds of this invention can be produced by introducing a mycoloyl group to the C-6 hydroxy group of benzyl N-acetylmuramide, followed by coupling the mycoloyl derivative with dipeptide benzyl ester and then by hydrogenolytical deprotection. More details of procedure are described hereinafter.

Carboxyl group of the starting material, i.e., benzyl N-acetyl-α-muramide (II) is protected by a suitable protective group such as diphenylmethyl group. This protection of carboxyl group in compound (II) is not essential but expected to prevent undesirable side-reaction in subsequent steps. Next, the C-6 hydroxy group of compound (III), if desired, is activated by treating with tosyl chloride or methanesulfonyl chloride in a basic solvent such as pyridine.

Then, the compound (IV) is allowed to react with alkali metal mycolate in a suitable polar solvent such as dimethylformamide or dimethylsulfoxide at the temperature of about 100° to 140° C. The reaction can proceed smoothly when the reaction is conducted in a non-polar solvent such as benzene in the presence of a catalytical amount of a cyclic polyether compound such as 18-Crown-6.

The protective group of carboxyl group of compound (V) thus obtained is removed, for example, with trifluoroacetic acid and the product (VI) obtained is allowed to react with dipeptide moiety such as L-alanyl-D-isoglutamine benzyl ester in the presence of a suitable condensating agent such as dicyclohexylcarbodiimide and N-hydroxysuccinimide. This reaction is usually conducted under stirring in a suitable non-polar solvent such as ethyl acetate, benzene, dioxane or tetrahydrofuran at room temperature. Finally, protective groups of compounds (VII) are removed to obtain object compound (I) by means of a conventional method, for example, by hydrogenating in the presence of palladium black or platinum or by treating with a solution of hydrobromic acid in acetic acid.

The object compound may be also prepared by reaction of the compound (II) with dipeptide moiety followed by reaction of the compound resulted with a mycolic acid or a synthetic fatty acid.

One of the starting materials, mycolic acid, can be produced by a conventional method described hereinafter. That is, mycolic acid can be obtained by hydrolyzing whole bacilli, wax-D preparation (peptideglycolipid) or tightly-bound-lipid preparation of various kinds of bacteria and purifying the hydrolyzed products with active aluminum or silica gel chromatography. Mycolic acid is basically defined by Asselineau as a higher fatty acid having both a long branched chain of alkyl group on the α-position thereof and hydroxy group on the β-position thereof (Asselineau J; The bacterial Lipids Hermann Paris 1996). Mycolic acid used in this invention, however, can be a single or a mixture of higher fatty acid having total carbon number of $C_{28}$-$C_{90}$, the α-position of which is substituted with a long branched chain of alkyl group and the β-position of which is substituted with hydroxy group.

The preparation thus obtained is usually a mixture of several kinds of mycolic acid and if necessary, a single mycolic acid may be isolated by further purification. However, from the view point of the biological activity in this invention, complete purification to a single mycolic acid is not essential and such mixture of several kinds of mycolic acid is sufficient for the use.

Generally, one of the higher class of mycolic acid, that is, mycomycolic acid can be obtained from human-type, bovine-type or avian-type of Mycobacterium tuberculosis, *M.phlei, M.smegmatis*, which are higher fatty acid having total carbon number of about 70–90 and at least having both a long branched chain of alkyl group ($C_{22}$–$C_{24}$) on the α-position and a hydroxy group on the β-position thereof.

On the other hand, as a middle class of mycolic acid, nocardomycolic acid, corynomycolic acid or arthrobactermycolic acid and the like may be listed, which is a middle fatty acid having total carbon number of about 28–70 and at least having both a long branched chain of alkyl group ($C_8$–$C_{16}$) on the the α-position and a hydroxy group on the β-position thereof.

As a bacteria of Nocardia genus to obtain nocardomycolic acid, *Nocardia asteroides, N.rubra, N.brasiliensis* or *N.Polychromogenes* and the like can be used.

As a bacteria of Corynobacterium genus and Arthrobacter genus to obtain *Corynomycolic acid, Coryno diphtheriae, C.pseudotuberculosis, C.xerosis, C.renale, Arthrobacter simplex, A.flavescens* and the like can be used. The compounds thus obtained of this invention have adjuvant activity in the induction of delayed-type hypersensitivity as well as that of muramyldipeptide and shows cell-mediated cytotoxic activity and antitumor activity which is not recognized in muramyldipeptide. Therefore, the object compound of this invention can be sufficiently anticipated for an immunotherapic agents of cancer of human being and animals, as expected with cell wall or the cell wall skeleton of BCG and the other mycobacteria or nocardia. Further, the object compounds of this invention have the following characteristics.

(a) The compounds of this invention have a simple and definite structure in comparison with bacterial cell wall or its cell wall skeleton, therefore can be synthetically prepared in highly pure uniform component as possible in chemicals.

(b) As the object compound of this invention can be suspended with phosphate buffered saline, the suspension may be administered intravenously without any severe side effect. While, an intradermal or intramuscular injection of oil-in-water suspension of cell wall skeleton of bacteria, from which such uniform suspension can not be prepared, may give side effect such as severe tissue reaction inavoidably.

(c) The object compounds of this invention have less possibility of having antigenic properties, than those of conventional immunoadjuvant substances as recognized in Freund's complete adjuvant. To demonstrate superiority, the pharmacological properties of several representative compounds of this invention were compared with those of muramyldipeptide and stearoyl muramyldipeptide which are structually similar to the object compound of this invention.

The results were summarized as in the following Tables. In Table 1 to 3, the compounds of this invention is abbreviated as follows;

6-O-mycomycoloyl-N-acetylmuramyl-L-alanyl-D-isoglutamine obtained in Example 1 = myco-L-Ala-D-isoGln.

6-O-nocardomycoloyl-N-acetylmuramyl-L-alanyl-D-isoglutamine obtained in Example 2 = nocardo-L-Ala-D-isoGln 6-O-corynomycoloyl-N-acetylmuramyl-L-alanyl-D-isoglutamine obtained in Example 3 = coryno-L-Ala-D-isoGln 6-O-mycomycoloyl-N-acetylmuramyl-glycyl-D-isoglutamine obtained in Example 4 = myco-Gly-D-isoGln 6-O-mycomycoloyl-N-acetylmuramyl-L-ser-D-isoglutamine obtained in Example 5 = myco-L-Ser-D-isoGln Table 1

Adjuvant activity of the object compound on the induction of delayed-type hypersensitivity to ABA-Tyr.

| Material | Dose (μg/mice) | Skin reaction with 100μg of ABA-BαA at 24 hrs. (mm ± SE) |
|---|---|---|
| Myco-L-Ala-D-isoGln | 500 | 20.9 ± 0.8 |
|  | 50 | 22.8 ± 0.6 |
| Muramyldipeptide | 100 | 22.5 ± 0.5 |
| Stearoyl-muramyldipeptide | 100 | 17.2 ± 1.2 |
| Control (ABA-Tyr alone) | 0 | 0 |
| Nocardo-L-Ala-D-isoGln | 400 | 23.0 ± 1.5 |
|  | 40 | 24.5 ± 0.7 |
| Coryno-L-Ala-D-isoGln | 300 | 22.0 ± 0.6 |
|  | 30 | 21.2 ± 1.9 |
| Muramyldipeptide | 100 | 24.0 ± 0.7 |
| Control (ABA-Tyr alone) | 0 | 0 |
| Myco-L-Ser-D-isoGln | 500 | 15.0 ± 0.5 |
|  | 50 | 18.0 ± 0.6 |
| Myco-L-Ala-D-isoGln | 500 | 17.1 ± 0.5 |
|  | 50 | 12.8 ± 1.6 |
| Muramyldipeptide | 100 | 17.5 ± 1.2 |
| Control (ABA-Tyr alone) | 0 | 0 |
| Myco-Gly-D-isoGln | 500 | 15.3 ± 0.6 |
|  | 50 | 2.7 ± 0.7 |
| Muramyldipetide | 100 | 22.8 ± 1.5 |
| Control (ABA-Tyr-alone) | 0 | 0 |

Hartley guinea pigs were immunized into four foot-pads with 50 μg of N-acetyl-L-tyrosine-3-azobenzene-4'-arsonic acid (ABA-Tyr) in Freund's incomplete adjuvant with a test material dissolved or suspended in phosphate buffered saline. Control groups were immunized with ABA-Tyr alone in Freund's incomplete adjuvant.

Two weeks later, skin test with 100 μg of ABA-bacterial α-amylose (ABA-BαA) dissolved in saline was made and skin reaction was measured 24 hours after intradermal injection of test antigen.

Table 2

Adjuvant activity on the induction of cell-mediated cytotoxic cells in the spleen of allogenic mice (C57BL/6J).

| Material | Dose (μg/mice) | Administering Form | Specific Target Cell Lysis (%) |
|---|---|---|---|
| Myco-L-Ala-isoGln | 100 | Phosphate buffered saline suspension | 69.7 |
|  | 10 |  | 3.9 |
| Muramyl dipeptide | 100 |  | 2.2 |
|  | 10 |  | 2.0 |
| Stearoyl muramyldipeptide | 100 |  | 4.2 |
| Control | 100 |  | 2.5 |
| Nocardo-L-Ala-D-isoGln | 100 |  | 76.9 ± 3.2 |
|  | 10 |  | 21.0 ± 7.6 |
| Coryno-Ala-D-isoGln | 100 |  | 28.8 ± 14.4 |
|  | 10 |  | 16.1 ± 5.0 |
| Myco-Gly-isoGln | 100 |  | 77.0 ± 4.0 |
|  | 10 |  | 39.3 ± 3.2 |
| Myco-L-Ser-D-isoGln | 100 |  | 30.4 ± 14.0 |
|  | 10 |  | 21.8 ± 15.2 |
| Muramyldipeptide | 100 |  | 11.1 ± 0.5 |
| Control | 100 |  | 10.3 ± 0.7 |

Three or four mice of C57BL/6J in each group were immunized intraperitoneally with a mixture of mastocytoma P815-X2 cells (1 × 10⁴) and a test material dissolved or suspended in phosphate buffered saline. Control group was immunized with mastocytoma P815-X2 cells alone.

Eleven days after, cell-mediated cytotoxicity was determined by Brunner's method (Immunology 18, 501–515 1970). As shown in Table 2, the object compound of this invention showed strong adjuvant activity in mice which were immunized with mastocytoma P815-X2 cells.

Table 3

Antitumor activity on the suppression of MH-134 hepatoma in C3H/He mice

| Material | Dose (μg) | Antitumor Activity A/B* Tumor Growth |
|---|---|---|
| Myco-L-Ala-D-isoGln | 100 | 10/10 |
| Nocardo-L-Ala-D-isoGln | 20 | 5/10 |
| Coryno-L-Ala-D-isoGln | 20 | 6/10 |
| Myco-L-Ser-isoGln | 100 | 10/10 |
| Myco-Gly-D-isoGln | 100 | 7/10 |
| Muramyldipeptide | 20 | 0/10 |
|  | 100 | 0/10 |
| Stearoyl muramyldipeptide | 20 | 0/10 |
|  | 100 | 0/10 |
| Control (phosphate buffered-saline-alone) |  | 0/10 |

*A = Number of mice whose tumor growth were completely suppressed.
*B = Number of tested mice.

The antitumor activity of the compounds of this invention was examined by using MH134 hepatoma in syngeneic C3H/He mice. A mixture of tumor cells of MH134 (1 × 10⁵) and materials (100 or 20 μg) dissolved or suspended in phosphate buffered saline and transplanted intradermally into C3H/He mice and the tumor growth was measured in inoculated sites.

As shown in Table 3, the phosphate-buffered saline solution or suspension of the object compounds of this invention potently suppressed the tumor growth in syngenic mice in comparison with muramyldipeptide and 6-0-stearoyl-muramyldipeptide.

Preparation of several kinds of mycolic acid as one of the starting material for the synthesis of the object compounds. 1. Wax D, whole bacilli, cell wall and cell wall skeleton of Mycobacterium tuberculosis strain Aoyama B was hydrolyzed with alkali and subjected to column chromatography on activated alumina to obtain mycolic acid.

To 5 ml of Chloroform having dissolved therein 0.50 g of mycolic acid was added a drop of a 1% phenolphthalein solution and the mixture was titrated with a 0.2 N methanolic KOH solution, which was required in an amount of 2.405 ml. From this it followed that the average molecular weight of the mycolic acid as a monobasic acid amounted to 1186.

After the concentration under reduced pressure methanol was added to the above residue and insoluble substances were removed by filtration to obtain 0.51 g of potassium mycolate.

Yield: 98% Melting Point: 71° - 83° C

Elemental analysis of the mycolic acid was as follows.

| Elemental Analysis | | |
|---|---|---|
| (1) | C 81.57% | H 13.48% |
| (2) | C 81.33% | H 13.62% |
| Average | C 81.45% | H 13.55% |

From the average molecular weight obtained by titration and that obtained by elemental analysis average molecular formula of mycolic acid was determined to be $C_{80}H_{158}O_{3.5}$ = 1176. 2. Whole bacilli of Nocardia asteroides 131 was hydrolyzed with alkali, esterified (methyl esterification), purified with column chromatography on silica gel and then hydrolyzed to obtain middle mycolic acid.

A mixture of 1.24 g of the middle mycolic acid (nocardomycolic acid) and 2 ml of a 3N methanolic KOH solution was heated under reflux for 2.5 hours. After the concentration under reduced pressure the residue was dissolved in 100 ml of diethyl ether and washed with 1N aqueous hydrochloric acid solution and then with water. The solution was dried over dehydrated MgSO$_4$ followed by concentrating under reduced pressure. The residue thus obtained was washed with ice cooled ethanol and dried over phosphorus pentoxide under reduced pressure to obtain 0.89 g of waxy product.

Yield: 73%
Elemental Analysis C 79.69%, H 12.76%

To 10 ml of chloroform having dissolved therein 870 mg of nocardomycolic acid thus obtained was added a drop of a 1% phenolphthalein solution and the mixture was titrated with a 0.5 N methanolic KOH solution ($f$ = 0.92), which was required in an amount of 2.465 ml. From this the average molecular weight of nocardomycolic acid as a monobasic acid was calculated to be 767. The above solution was concentrated under reduced pressure and dissolved in diethyl ether followed by filtering under suction. Then, the filtrate was concentrated under reduced pressure to obtain 0.88 g of waxy product. Yield: 98%.

From the elemental analysis and average molecular weight obtained above, the molecular formula of nocarbonycolic acid was determined to be $C_{51}H_{97}O_{3.6}$ = 768 3. Whole bacilli of Corynobacterium diphtheriae PW8 was treated as the same manner in Nocardia asteroides 131 to obtain middle mycolic acid.

A mixture of 0.53 g of methyl ester of the middle mycolic acid (Corynomycolic acid) and 2 ml of a 3N methanolic KOH solution was heated under reflux for 2.5 hours. After the concentration under reduced pressure, the residue was dissolved in 15 ml of diethyl ether, washed with a 1N aqueous HCl solution and then with water. The solution was dried over dehydrated MgSO$_4$ followed by concentrating under reduced pressure. The residue thus obtained was dissolved in a small amount of methanol. After cooling, there precipitated waxy product, which was removed by decantation. Then, it was washed with cold methanol and dried under reduced pressure to obtain 0.41 g of waxy product. Yield: 80%.

Elemental Analysis C 76.48% H 12.69%

To 5 ml of chloroform having dissolved therein 385 mg of corynomycolic acid was added a drop of phenolphthalein and the mixture was titrated with a 0.50 N methanolic KOH solution ($f$ = 1.00), which was required in an amount of 1.47 ml. From this the average molecular weight of corynomycolic acid as a monobasic acid was calculated to be 524. Further, the above solution was concentrated under reduced pressure and dissolved in diethyl ether followed by filtering under suction. Then, the filtrate was concentrated under reduced pressure to obtain 412 mg of waxy product. Yield: 99%.

From the elemental analysis and average molecular weight obtained above, the molecular formula of corynomycolic acid was determined to be $C_{33}H_{66}O_{3.5}$ = 519.

EXAMPLE 1

To 1.0 g of benzyl-N-acetyl-α-muramide dissolved in 10 ml of tetrahydrofuran, was added 0.8 g of diphenyldiazomethane. The mixture was stirred at room temperature for 30 minutes. After removal of the solvent, the residue was crystallized on trituration with hexane.

Recrystallization was effected from a mixture of ethyl acetate and hexane to give 1.3 g of 1-α-O-benzyl-N-acetylmuramic acid diphenylmethyl ester. The crystal was again recrystallized from the same solvent to give pure crystal having a melting point of 155° C – 156° C; $[\alpha]_D^{22}$ + 122° C (c 1.0, CHCl$_3$)

Elemental Analysis for $C_{31}H_{35}O_8N$ Calcd C 67.74% H 6.42% N 2.55% Found C 67.62% H 6.50% N 2.52%

In 3 ml of pyridine 0.3 g of 1-α-O-benzyl-N-acetylmuramic acid diphenymethyl ester was dissolved. To the solution, was added 1.2 g of tosyl chloride and the solution was stirred for one hour. The solution was poured into water and extracted with ethyl acetate. The ethyl acetate solution was washed successively with 0.3 N sodium hydroxide solution, water, 1 N hydrochloric acid solution and water and then dried on magnesium sulfate. After distillation of the solvent in vacuo, the residue was purified by silica gel (10 g) column chromatography. Elution with benzeneethyl acetate (5:1) gave a fraction containing 0.34 g of pure 1-α-O-benzyl-6-tosyl-N-acetylmuramic acid diphenylmethyl ester having a melting point of 68-73° C; $[\alpha]_D^{22}$ + 84.4° (c 0.5, CHCl$_3$)

Elemental Analysis for $C_{38}H_{41}O_{10}NS$ Calcd C 64.85% H 5.87% N 1.99% S 4.56% Found C 64,68% H 5.92% N 1.93% S 4.31%

Potassium mycomycolate (0.38 g) was added to a solution of 0.33 g of 1-α-O-benzyl-6-O-tosyl-N-acetylmuramic acid diphenylmethyl ester and 0.02 g of 18-crown-6 in 10 ml of benzene, and the mixture was refluxed for 3 hours.

After removal of the solvent in vacuo, the residue was washed with acetone. The insoluble materials were subjected to a silica gel column chromatography.

Eluate with a mixture of benzene and ethyl acetate (10:1 V/V) was treated with an etherial solution of diazomethane at room temperature. Methyl esterification of excess mycolic acid facilitated the chromatographic purification of the object compound. After removal of the solvent in vacuo, the residue was again subjected to silica gel column chromatography. After elution of methyl mycolate with benzene, eluate with a mixture of benzeneethyl acetate (10:1) was collected. After removal of the solvent, the residue was recrystallized from acetone to give 0.32 g of 1-α-O-benzyl-6-O-mycomycoloyl-N-acetylmycomuranic acid diphenylmethyl ester having a melting point of 54°-57° C. $[\alpha]_D^{22} + 32.6$ (C=0.5 CHCl$_3$)

Elemental analysis for $C_{111}H_{191}O_{10.5}N$ Calcd C 78.07% H 11.27% N 0.82% Found C 78.34% H 11.48% N 0.85%

A mixture of 0.3 g of 1-α-O-benzyl-6-O-mycomycoloyl-N-acetylmuramic acid diphenylmethyl ester and 1 ml of anisole was dissolved in 20 ml of chloroform.

To the ice-cooled solution, 3.0 ml of trifluoroacetic acid was added. After stirring for 30 minutes acetone was added to the reaction mixture and the solvent was removed in vacuo. The residue was washed with ethanol and dissolved in 10 ml of tetrahydrofuran.

To this solution, 75 mg of N-hydroxysuccinimide, 65 mg of L-alanyl-D-isoglutamine benzyl ester hydrochloride, 24 mg of triethylamine dissolved 0.2 ml of tetrahydrofuran and 37 mg of dicyclohexylcarbodiimide were added under stirring in an ice bath. Stirring was continued overnight, allowing the temperature of the mixture to reach to room temperature.

Triethylamine hydrochloride and N,N'-dicyclohexylurea formed were filtered off. After evaporation of the solvent in vacuo, materials soluble in ethanol were removed and the residue was chromatographed on silica gel. Eluate with a mixture of benzeneacetone (3:1) was collected and the solvent was evaporated.

The residue was recrystallized from a mixture of benzene and methanol to give 0.124 g of 1-α-O-benzyl-6-O-mycomycoloyl-N-acetylmuramyl-L-alanyl-D-isoglutamine benzyl ester having a melting point of 171 - 172° C. $[\alpha]_D^{22} + 30.2$ (c 0.5, CHCl$_3$)

Elemental Analysis for $C_{113}H_{200}N_{13.5}N_4$ Calcd C 74.13% H 11.01% N 3.06% Found C 73.63% H 11.05% N 3.18%

1-α-O-Benzyl-6-O-mycomycoloyl-N-acetylmuramyl-L-alanyl-D-isoglutamine benzyl ester (76 mg) was dissolved in 20 ml of tetrahydrofuran and hydrogenolyzed in the presence of palladium black at room temperature. After the reaction, the solvent was removed in vacuo. The residue was recrystallized from a mixture of ether and ethanol to give 64 mg of 6-O-mycomycoloyl-N-acetylmuramyl-L-alanyl-D-isoglutamine having a melting point of 137°-160° C.

$[\alpha]_D^{22} + 24.3°$ C (after 9 min. c 0.4, THF-H$_2$O 50:1) + 25.8 (after 20 hrs. c 0.4, THF-H$_2$O 50:1)

Elemental Analysis for $C_{99}H_{188}N_{13.5}N_4 \cdot H_2O$ Calcd C 71.26% H 11.48% N 3.36% Found C 71.08% H 11.40% N 3.26%

EXAMPLE 2

1-α-O-Benzyl-N-acetylmuramic acid diphenylmethyl ester (0.48 g) and 0.03 g of 18-crown-6 were added to 15 ml of benzene. To the solution, was added 0.31 g of potassium corynomycolate and the solution was refluxed for 3 hours.

After cooling, the reaction mixture was washed with 0.1N hydrochloric acid and water and then dried. After evaporation of the solvent in vacuo, the residue was subjected to a silica gel column chromatography. Eluate with a mixture of benzene and ethyl acetate (5:1) was concentrated to give 0.30 g of 1-α-O-benzyl-6-O-corynomycoloyl-N-acetylmuramic acid diphenylmethyl ester.

$[\alpha]_D^{25} + 58.4°$ (c 1.0, CHCl$_3$)

Elemental Analysis for $C_{64}H_{99}O_{10.5}N$ Calcd C 73.17% H 9.50% N 1.33% Found C 72.85% H 9.27% N 1.40%

1-α-O-Benzyl-6-O-corynomycoloyl-N-acetylmuramic acid diphenylmethyl ester (0.22 g) and 0.1 ml of anisole were dissolved in 10 ml of dichloromethane.

To the ice-cooled solution, 1.6 ml of trifluoroacetic acid was added. After stirring for 30 minutes, the solvent was removed in vacuo. The residue was subjected to silica gel column chromatography. After elution of anisole and diphenylmethanol resulted as by-product with a mixture of benzene and ethyl acetate (5:1), eluate with a mixture of chloroform and methanol (5:1) was collected and the solvent was removed in vacuo to obtain 1-α-O-benzyl-6-O-corynomycoloyl-N-acetylmuramic acid. To this product, was added 89 mg of L-alanyl-D-isoglutamine benzyl ester hydrochloride and 0.036 ml of triethylamine in 5 ml of tetrahydrofuran. The mixture was cooled in an ice-salt bath (−15°) and 42 mg of N-hydroxysuccinimide and 46 mg of dicyclohexylcarbodiimide were added. The mixture was stirred for one hour at the same temperature and stirring was continued overnight at room temperature.

Triethylamine hydrochloride and N,N'-dicyclohexylurea formed were filtered off. After evaporation of the solvent, the residue was washed with a mixture of methanol and water (1:1) and with ether.

Recrystallization from a mixture of methanol and water gave 0.13 g of 1-α-O-benzyl-6-O-corynomycoloyl-N-acetylmuramyl-L-alanyl-D-isoglutamine benzyl ester having a melting point of 172°-174° C $[\alpha]_D^{14} + 53.7°$ C (c 1.0, CHCl$_3$)

Elemental Analysis for $C_{66}H_{108}O_{13.5}N_4$ Calcd C 67.54% H 9.28% N 4.77% Found C 67.50% H 9.10% N 5.01%

1-α-O-Benzyl-6-O-corynomylcoloyl-N-acetylmuramyl-L-alanyl-D-isoglutamine benzyl ester (105 mg) was dissolved in 8 ml of tetrahydrofuran.

The solution was subjected to hydrogenolysis in the presence of palladium black at 28° C.

After the reaction, the solvent was removed in vacuo. The residue was recrystallized from a mixture of methanol, ether and acetone to obtain 59 mg of 6-O-corynomycoloyl-N-acetylmuramyl-L-alanyl-D-isoglutamine having a melting point of 152° to 155° C.

$[\alpha]_D^{11} + 31.9°$ C (c 0.89, tetrahydrofuran-H$_2$O=50:1, after 46 hrs.)

Elemental Analysis for $C_{52}H_{96}O_{13.5}N_4 \cdot 2.5H_2O$. Calcd C 60.14% H 9.80% N 5.40% Found C 59.81% H 9.60% N 5.29%

EXAMPLE 3

From 0.35 g of 1-α-O-benzyl-N-acetylmuramic acid diphenylmethyl ester and 0.31 g of potassium nocardomycolate, 0.34 g of 1-α-O-benzyl-6-O-nocardomycoloyl-N-acetylmuramic acid diphenylmethyl ester was obtained in the same manner as in Example 2.

$[α]_D^{27}$ + 46.7° (c 1.0, $CHCl_3$)

Elemental Analysis for $C_{82}H_{130}O_{10.6}N_1$ Calcd C 75.79% H 10.08% N 1.08% Found C 75.38% H 10.15% N 1.03%

After treatment of 1-α-O-benzyl-6-O-nocardomycoloyl-N-acetylmuramic acid diphenylmethyl ester (0.24 g) with trifluoroacetic acid, the free carboxylic acid was coupled with 75 mg of L-alanyl-D-isoglutamine benzyl ester hydrochloride in the same manner as in Example 2 to obtain 0.14 g of 1-α-O-benzyl-6-O-nocardomycoloyl-N-acetylmuramyl-L-alanyl-D-isoglutamine benzyl ester having a melting point of 164°–167° C.

$[α]_D^{17}$ + 44.7 (c 1.0, $CHCl_3$)

Elemental Analysis for $C_{84}H_{139}O_{13.6}N_4$. Calcd C 70.91% H 9.85% N 3.94% Found C 70.99% H 9.92% N 3.92%

The above compound (84 mg) was subjected to hydrogenolysis in the same manner as in Example 2 to obtain 51 mg of 6-O-nocardomycoloyl-N-acetylmuramyl-L-alanyl-D-isoglutamine having a melting point of 154° to 157° C (decomposition).

$[α]_D^{20}$ + 30.0° (c 1.03, tetrahydrofuran-$H_2O$=50:1 after 24 hours).

Elemental Analysis for $C_{70}H_{127}O_{13.6}N_4 \cdot 1.5H_2O$. Calcd C 66.22% H 10.32% N 4.41% Found C 66.07% H 10.58% N 4.26%

EXAMPLE 4

A mixture of 1-α-O-benzyl-6-O-mycomycoloyl-N-acetylmuramic acid diphenylmethyl ester and 0.2 ml of anisole were dissolved in 20 ml of dichloromethane. To the solution, was added 3 ml of trifluoroacetic acid. After stirring the solution for 30 minutes, the solvent was removed in vacuo. The residue was subjected to silica gel column chromatography. After elution of anisole and diphenylmethanol resulted as by-product with a mixture of benzene and ethyl acetate (5:1), eluate with a mixture of chloroform and methanol (5:1) was collected and the solvent was removed in vacuo to obtain 1-α-O-benzyl-6-O-mycomycoloyl-N-acetylmuramic acid.

To this product was added 0.15 g of O-benzyl-L-seryl-D-isoglutamine benzyl-ester hydrochloride and 0.05 ml of triethylamine dissolved in 10 ml of tetrahydrofuran and the solution was cooled to −10° C.

Then, 50 mg of N-hydroxysuccinimide and 69 mg of dicyclohexylcarbodiimide were added under stirring for one hour at the same temperature and further stirred overnight at room temperature. Triethylamine hydrochloride and N,N'-dicyclohexylurea formed as by-product were filtered off and the solvent was removed by distillation. The residue was subjected to silica gel column chromatography.

Eluate with a mixture of chloroform and methanol (30:1) was collected and the solvent was removed. The residue was recrystallized from a mixture of benzene and methanol to give 0.35 g of 1-α-O-benzyl-O-mycomycoloyl-N-acetylmuramyl-O-benzyl-L-seryl-D-isoglutamine benzyl ester having a melting point of 164°–166° C.

$[α]_D^{25}$ + 32.1 (c 0.5, $CHCl_3$)

Elemental Analysis $C_{120}H_{206}O_{14.5}N_4$ Calcd C 74.39% H 10.74% N 2.89% Found C 74.41% H 10.59% N 2.87%

1-α-O-benzyl-6-O-mycomycoloyl-N-acetylmuramyl-O-benzyl-L-seryl-D-isoglutamine benzyl ester (0.2 g) thus obtained was dissolved in 20 ml of tetrahydrofuran and the solution was hydrogenolyzed in the presence of palladium black at room temperature.

After the reaction, the solvent was removed in vacuo. The residue was recrystallized from a mixture of tetrahydrofuran and methanol to give 0.14 g of 6-O-mycomycoloyl-N-acetylmuramyl-L-seryl-D-isoglutamine having a melting point of 114°–120° C (decomp) $[α]_D^{25}$ + 35.2° (c 1.0, tetrahydrofuran-$H_2O$=50:1 after 48 hours).

Elemental Analysis for $C_{99}H_{188}O_{14.5}N_4$ Calcd C 71.33% H 11.39% N 3.36% Found C 71.03% H 11.33% N 3.42%

EXAMPLE 5

Starting from 0.5 g of 1-α-O-benzyl-6-O-nocardomycoloyl-N-acetylmuramic acid diphenylmethyl ester, the same procedure as in Example 4 was followed to obtain 6-O-nocardomycoloyl-N-acetylmuramyl-L-seryl-D-isoglutamine having a melting point of 125°–130° C (decomp). $[α]_D^{25}$ + 32.2 (c 1.0, tetrahydrofuran-$H_2O$=50:1 after 48 hours).

Elemental Analysis for $C_{70}H_{127}O_{14.6}N_4 \cdot H_2O$ Calcd C 65.85% H 10.21% N 4.39% Found C 65.62% H 10.33% N 4.48%

EXAMPLE 6

To a solution of 0.5 g of sodium in 15 ml of anhydrous methanol, was added 3.6 g of diethyl malonate. After the solution had been stirred at 50° C for 20 minutes, 6.0 g of tetradecyl bromide was added to the solution at the same temperature and then refluxed for 5 hours. After cooling, ether was added to the solution. Sodium bromide resulted was filtered off and the solvent was removed by distillation. The resulting oil was added to 15 ml of anhydrous methanol containing 0.5 g of sodium. To the solution was further added 6.0 g of tetradecyl bromide. The solution was refluxed for 5 hours. After cooling, the solution was diluted with water and extracted with ether. The ether solution was washed with water and dried. After evaporation of the solvent, the residue was recrystallized from ethanol to obtain 6.7 g of diethyl 2,2-bistetradecylmalonate having a melting point of 30°–32° C. To a solution of 2.7 g of potassium hydroxide in a mixture of 10 ml of water and 20 ml of ethanol, was added 6.5 g of diethyl 2,2-bistetradecylmalonate. The solution was refluxed for 10 hours. After cooling, the solution was acidified with 3M sulfuric acid, and extracted with ether.

The ether solution was washed with water and dried. After evaporation of the solvent, the residue was heated at 190°–200° C for one hours and then recrystallized from methanol to obtain 4.9 g of 2-tetradecylhexadecanoic acid having a melting point of 73.5 – 75° C.

Elemental Analysis for $C_{30}H_{60}O_2$ Calcd C 79.57% H 13.36% Found C 79.57% H 13.35%

A solution of 1.0 g of 2-tetradecylhexadecanoic acid and 0.79 g of thionyl chloride in 5 ml of benzene was refluxed for 7 hours. After removal of benzene and thionyl chloride, anhydrous benzene was added to the residue and then benzene was removed by distillation. This procedure was repeated 3 times to remove thionyl chloride completely. The residue was recrystallized from anhydrous hexane to obtain 0.75 g of 2-tetradecylhexadecanoyl chloride having a melting point of 51°–53° C. To the solution of 0.85 g of 1-α-O-benzyl-N-acetylmuramyl-L-alanyl-D-isoglutamine benzyl ester in 35 ml of anhydrous pyridine, was added 4.9 g of 2-tetradecylhexadecanoyl chloride dissolved in 35 ml of anhydrous tetrahydrofuran at 17°–18° C. After 45 minutes, 20 ml of water was added and the solution was stirred for 35 minutes at room temperature. The solution was adjusted to pH 3 with 1 M hydrochloric acid and extracted with chloroform. The chloroform solution was washed with saturated brine, and dried. After removal of solvent, the residue was subjected to silica gel column chromatography. Eluate with a mixture of chloroform and methanol (20:1) was concentrated and the residue was recrystallized from methanol to obtain 0.75 g of 6-O-(2-tetradecylhexadecanoyl)-1-α-O-benzyl-N-acetylmuramyl-L-alanyl-D-isoglutamine benzyl ester having a melting point of 173°–174° C.

Elemental Analysis for $C_{68}H_{101}O_{12}N_4$ Calcd C 68.39% H 9.20% N 5.06% Found C 68.04% H 9.29% N 5.03%

A solution of 0.70 g of 6-O-(2-tetradecylhexadecanoyl)-1-α-O-benzyl-N-acetylmuramyl-L-alanyl-D-isoglutamine benzyl ester thus obtained in 15 ml of tetrahydrofuran, was stirred in the presence of palladium black under hydrogen atmosphere at 30° C for 15 days. The resulting product was subjected to silica gel column chromatography and eluted with a mixture of chloroform, methanol and acetic acid (95:5:3). The eluate was concentrated and the residue was dissolved in a mixture of dioxane and water (1:1). The solution was lyophilized to obtain 0.50 g of 6-O-(2-tetradecylhexadecanoyl)-N-acetylmuramyl-L-alanyl-D-isoglutamine having a melting point of 152°–155° C.

Elemental Analysis for $C_{49}H_{87}O_{12}N_4 \cdot 2H_2O$ Calcd C 61.16% H 9.74% N 5.82% Found C 61.10% H 9.60% N 5.83%

What is claimed is:

1. Muramyldipeptide derivatives represented by the general formula

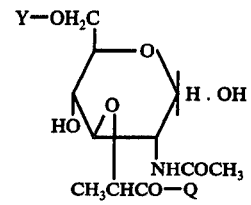

wherein Y represents a mycoloyl group or a synthetic higher acyl group having a total carbon number of $C_{30}$–$C_{90}$ and having at least a branched chain of long alkyl group on the α-position thereof; Q represents an -L-alanyl-D-isoglutamine group,
a -glycyl-D-isoglutamine group, or
an -L-seryl-D-isoglutamine group.

2. 6-O-mycomycoloyl-N-acetylmuramyl-L-alanyl-D-isoglutamine.

3. 6-O-corynomycoloyl-N-acetylmuramyl-L-alanyl-D-isoglutamine.

4. 6-O-nocardomycoloyl-N-acetylmuramyl-L-alanyl-D-isoglutamine.

5. 6-O-mycomycoloyl-N-acetylmuramyl-L-seryl-D-isoglutamine.

6. 6-O-nocardomycoloyl-N-acetylmuramyl-L-seryl-D-isoglutamine.

7. 6-O-(2-tetradecylhexadecanoyl)-N-acetylmuramyl-L-alanyl-D-isoglutamine.

8. The muramyldipeptide derivative of claim 1 wherein said long alkyl group at the α- position contains 8 to 25 carbon atoms.

9. The muramyldipeptide derivative of claim 1 wherein Y is a higher fatty acid having a total carbon number of about 70–90 with a long branch chain of an alkyl group of $C_{22}$–$C_{24}$ on the α-position thereof or has a total carbon number of about 28–70 with a long branch chain alkyl group ($C_8$–$C_{16}$) on the α- position thereof.

* * * * *